United States Patent [19]

Endo

[11] Patent Number: 5,034,320
[45] Date of Patent: Jul. 23, 1991

[54] VINBLASTINE SYNTHESIS
[75] Inventor: Tsuyoshi Endo, Sakyo, Japan
[73] Assignee: Allelix, Inc., Ontario, Canada
[21] Appl. No.: 32,459
[22] Filed: Mar. 31, 1987
[51] Int. Cl.$^5$ .................. C12P 17/18; C12N 9/04; C12N 9/08
[52] U.S. Cl. ..................... 435/119; 435/190; 435/192
[58] Field of Search .............. 435/117, 118, 119, 121, 435/190, 192; 540/478

[56] References Cited
PUBLICATIONS

Endo et al., "Biotransformation of Anhydrouinblastine to Vinblastine by a Cell-Free Extract of *Catharanthus roseus* Cell Suspension Cultures", Phytochemistry, vol. 26, 3233–3234, 1987.
Stich et al., "Investigation of Hydrogen Peroxide Formation in Plants", Phytochemistry, vol. 23, 2719–2722, 1984.
Stuart et al., "Studies on the Synthesis of Bisindole Alkaloids, Enzyme Catalysed formation of Heutosine", Heterocycles, vol. 9, 1015–1022, 1978.
Baxter et al., "Biosynthesis of the Antitumor Catharanthus Alkaloids, Conversion of an Hydrovinblastine to Vinblastine", J.C.S. Chem. Comm., vol. 6, pp. 257–259, 1979.

Goldberg et al., "The Final Stages of Lignin Biosynthesis", J. Exp. Bot., vol. 36 (164), 503–510, 1985.
Stuart et al., "Studies on the Biosynthesis of Bisindole Alkaloids, The Final Stages in Biosynthesis of Vinblastine, Heurosine and Catharine", Heterocycles, vol. 9 (10), 1391–1395, 1978.
McLauchlan et al., "Conversion of Anhydrovinblastine to Vinblastine by Cell-Free Homogenates of *Catharanthus roseus* cell Suspension Cultures", Tett., vol. 39, 3777–80, 1983.
Kutney et al., "Alkaloid Production in *Catharanthus roseus* Cell Cultures, Biotransformation of 3',4'-Anhydrovinblastine to Other Bisindole Alkaloids", vol. 65, 1271–78, 1982, Helvetica Chimica Acta.

*Primary Examiner*—Elizabeth C. Weimar
*Assistant Examiner*—Gail Poulos
*Attorney, Agent, or Firm*—Wyatt, Gerber, Burke & Badie

[57] ABSTRACT

The reaction of 3',4'-anhydrovinblastine with a *Catharanthus roseus*-derived protein fraction to form vinblastine is improved by conducting the reaction in the presence of a reducing agent such as the enzyme cofactor NADH. A cationic species such as manganous ion may also be added to the reaction. Vinblastine yields are enhanced.

5 Claims, No Drawings

VINBLASTINE SYNTHESIS

FIELD OF THE INVENTION

This invention relates to the production of the alkaloid dimer known as vinblastine.

BACKGROUND OF THE INVENTION

Vinblastine, also known as vincaleukoblastine, is an antitumor dimeric alkaloid produced by the plant *Catharanthus roseus*. According to the recent reports, the in vivo synthesis of vinblastine proceeds through an intermediate dimer 3', 4'-anhydrovinblastine which is generated when the monomers catharanthine and vindoline are properly coupled.

The 3', 4'-anhydrovinblastine (AVLB) which acts as precursor in the production of vinblastine according to the present process has only recently been identified and characterized. There are, however, recent publications which disclose methods for its isolation. For example, Canadian patent No. 1,094,552 issued Jan. 27, 1981 describes an extraction process by which AVLB is selectively separated using chromatography, from alkaloids precipitated en masse from ground *C. roseus* tissue e.g. dried leaves.

In J. Am. Chem. Soc./98:22/Oct. 27, 1976, Langlois et al describe a process in which the monomers catharanthine and vindoline are coupled to form AVLB. The coupling is performed using a peracid to generate first the N-oxide of catharanthine, followed by Polonovski-type fragmentation of the N-oxide initiated with addition of trifluoroacetic anhydride to form a dimer. A reducing agent such as sodium borohydride is then added to generate AVLB which can be isolated e.g. chromatographically.

Other methods for producing the precursor AVLB have been disclosed more recently. For example, copending U.S. patent application Ser. No. 685,704 filed Aug. 4, 1986 which issued on Oct. 18, 1988 as U.S. Pat. No. 4,778,885 discloses a process whereby catharanthine and vindoline are coupled in the presence of ferric ion. Copending U.S. patent application Ser. No. 893,018 filed Aug. 4, 1986, now U.S. Pat. No. 4,918,011 describes AVLB production through enzymatic coupling of catharanthine and vindoline, using peroxidase in the presence of a peroxide source.

Although it has recently been suggested that AVLB is itself a useful pharmaceutical, efficient production of AVLB has been sought largely as a means for enhancing yield of vinblastine.

Processes for converting AVLB to vinblastine have been proposed in the art. A review of numerous references indicates that, while purely chemical processes can be used to generate vinblastine and assist in understanding the in vivo transformation, a perhaps more promising method, in terms of vinblastine yield, relies on biotransformation. For example, in J. Am. Chem. Soc., 100:19, Sept. 3, 1978, Scott et al confirm that blank incubation of the monomers catharanthine and vindoline results in detectable amounts of dimers such as anhydrovinblastine, vinblastine and leurosine. Dimer yield is slightly increased when the monomers are fed to 6 week old *C. roseus* plants. In J.C.S. Chem. Comm., 1979, Baxter et al report on the ability to transform AVLB to vinblastine using cell-free extracts of *C. roseus* plants. A denatured extract exhibited little biotransformation activity indicating that components in the extract were responsible for vinblastine generation. Similar findings were reported by Kutney using *C. roseus* tissue cultures as extract source (see Helvetica Chimica Acta, Vol. 65m Fasc. 7 p. 2088-2101 (1982)) and by McLauchlan et al Tetrahedron, Vol. 39, No. 22, pp 3777-3780, 1983 who used a different line of cultured *C. roseus* cells as extract source.

While the component responsible for the conversion of AVLB to vinblastine has yet to be identified specifically, Kutney et al have produced data which indicated that a *C. roseus* fraction having a molecular weight greater than 25,000 is likely responsible for the biotransformation of the catharanthine and vindoline monomers to vinblastine (see Helvetica Chimica Acta, Vol. 65m Fasc. 7 p. 2088-2101 (1982)). Experimental evidence provided in this paper indicates that direct incorporation of radiolabelled 3', 4'-anhydrovinblastine into vinblastine using *C. roseus*-derived protein fraction as catalyst was around 1.8% when incubated at pH 6.3 and room temperature. Clearly, however, greater vinblastine yields are required before processes of this type can be considered economically viable.

In is therefore an object of the present invention to provide a novel process for preparing vinblastine.

It is a further object of the present invention to provide a process for preparing vinblastine in improved yield.

SUMMARY OF THE PRESENT INVENTION

As with the prior art processes, the present invention relies on exposure of the staring material 3', 4'-anhydrovinblastine to enzyme. In accordance with the present invention, however, the reaction is complemented with an effective amount of a reducing agent. Addition of reducing agent to the reaction has resulted in much improved vinblastine yields e.g. up to 12% in specific embodiments described herein.

Thus, according to one aspect of the present invention there is provided a method for preparing vinbastine which comprises reacting 3', 4'-anhydrovinblastine with enzyme and reducing agent.

In accordance with another aspect of the present invention, it has been found that reaction of enzyme and reducing agent to produce vinblastine is enhanced when a cationic species is added to the reaction.

Thus, according to a second aspect of the present invention there is provided a method for preparing vinblastine which comprises reacting 3', 4'-anhydrovinblastine with enzyme, reducing agent and cation.

For brevity herein, 3', 4'-anhydrovinblastine is referred to simply as AVLB.

DETAILED DESCRIPTION OF THE PREFERRED EMBODIMENTS

The AVLB used as starting material may be prepared in accordance with techniques described in the art as set out previously hereinabove.

Enzyme useful herein is able to convert 3', 4'-anhydrovinblastine to vinblastine in the absence of added reducing agent. The enzyme is preferably derived from *C. roseus* tissue such as leaves, cultured tissue and especially suspension cells which are either fresh or have been deep frozen. In general, any extraction method which recovers the majority of proteinaceous material from *C. roseus* tissue may be used provided that sufficient care is taken to maintain enzyme activity in the extract.

For example, the extraction method summarized in (see Helvetica Chimica Acta, Vol. 65m Fasc. 7 p. 2088-2101 (1982), may be used. In this method, *C. roseus* leaves are homogenized in 0.1M phosphate buffer at pH 6.3. The homogenate is then centrifuged at 30,000 g for 20 minutes and the supernatant recovered as a crude enzyme fraction containing proteins ranging in weight from 15,000 to 450,000 D. Subsequent fractionation and further purification may then be performed using, for example, anionic exchange chromatography e.g. with DEAE-cellulose, and/or molecular size sieves e.g. Sephadex G-200.

It is particularly preferred herein to use deep frozen suspension cells of *C. roseus* as enzyme source and to grind the cells in tris-HCl buffer at a mildly acidic pH. In addition, use of a phenolics precipitating agent such as polyvinylpyrrolidone has proved useful as a means of removing phenolics from the enzyme fraction.

Thus, a method which is preferred herein for producing enzyme useful in the reaction of the present invention comprises grinding frozen ($-20°$ C.) suspension cells in a chilled mortar containing polyvinylpyrrolidone and buffer at mildly acidic pH. The extract is centrifuged and the soluble protein is precipitated such as by treatment with ammonium sulphate. Collected protein precipitate is then desalted and either used directly or stored in the cold e.g. $-20°$ C. for later use.

In the prior art processes, the recovered enzyme fraction is incubated with AVLB to produce vinblastine. In accordance with the present invention, incubation of AVLB and enzyme is supplemented with a reducing agent to encourage vinblastine formation to an extent greater than is possible when reducing agent is not present.

Reducing agents useful herein may be selected from a variety of organic and inorganic agents although organic reducing agents are preferred, given the biochemical nature of the reaction and the reactants. Considering the proteinaceous nature of the enzyme fraction, it is suggested that strong bases not be used as reducing agents.

It has been found that the cofactors are most useful in the reaction. Thus, preferred reducing agents for use herein include riboflavin-based derivatives and nicotinic acid-based derivatives such as flavin mononucleotide (FMN), flavin adenine dinucleotide (FAD) nicotinamide adenine dinucleotide (NAD) and its phosphate analogue NADP. In particular, the reduced forms of these cofactors i.e. $FMNH_2$, $FADH_2$, NADH and NADPH are preferred for use therein. Other cofactors used herein include vitamin $B_{12}$ and reduced coenzyme Q. Best results have been obtained with NADH and its use is therefore most preferred herein.

As is generally known, reduction of a substrate by NADH results in oxidation of NADH to $NAD^+$. In order to maintain a supply of reducing NADH equivalents, the present invention comprises the use of additional agents to continuously regenerate the NADH pool in the reaction. Methods and agents for accomplishing this will be apparent to those skilled in this art. For example, an oxidizable substrate and a dehydrogenase enzyme which acts thereon may be used such as, in combination, lactate and lactate dehydrogenase or formate and formate dehydrogenase or pyruvate and pyruvate dehydrogenase. Reactions of this type will regenerate NADH as long as the oxidizable substrate is present. Accordingly, in those instances in which long reaction runs are desired, oxidizable substrate is added to the reaction as required, the respective dehydrogenase being present in the reaction medium in an amount which can be predetermined. The overall reaction contemplated by this embodiment of the invention is represented below:

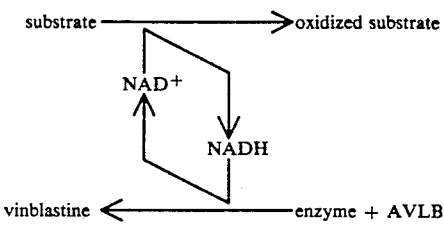

The capacity to replenish the NADH pool is not always necessary. Shorter reaction times are suitable herein and do not require regeneration of NADH to obtain efficient vinblastine transformation. The controlling factor in this regard will be the amount of AVLB used as starting material. Relatively large amounts of AVLB may require the concomitant use of large amounts of enzyme and NADH. In this case, the initial amount of NADH added to the reaction can be lower in the case where the NADH regeneration scheme described above is employed.

The ability of the reducing cofactor to increase vinblastine yield is enhanced by the addition of a cationic species to the reaction. Preferred cationic species include the divalent inorganic cations such as calcium, magnesium, cobalt, zinc, copper, nickel and manganese. Especially preferred is manganese when the reducing agent selected for use is NADH. The source of the cation is preferably a water soluble salt thereof.

Transformation of anhydrovinblastine to vinblastine is accomplished, in accordance with the present invention, by incubating AVLB with enzyme and reducing agent. More preferably, AVLB is incubated with a *C. roseus*-derived protein fraction, NADH and $MnCl_2$ at a temperature around room temperature although the temperature may range between $0°$ C. and about $80°$ C. i.e. a temperature at which enzyme activity is maintained.

The relative amounts of reagents may vary widely. for example, an initial amount of AVLB is suitably reacted with at least an equivalent amount of *C. roseus* protein by dry weight. The reaction kinetics are desirably enhanced by the addition of excess enzyme, however, and addition of excess enzyme is therefore preferred. The amount of cofactor added is also suitably equivalent to the amount of AVLB in the reaction vessel.

Although all reactants may be added at the same time, control of reaction initiation is more desirable. This may be accomplished, for example, by adding the cofactor as the final ingredient once AVLB, enzyme and any desired amount of cation are admixed, for example, in a buffer such as tris-HCl, HEPES, phosphate, MES or the like. The pH of the reaction medium, after reagent addition, may range from about pH 4 to pH 9. Best results to date have been obtained when operating within a pH in the range from mildly acidic to mildly basic e.g. from pH 6.5 to pH 8.0.

The need for an adequate supply of reducing agent e.g. NADH, is apparent from some experimental data presented herein. It has been found that timely additions of portions of the total cofactor desired in the reaction has enhanced reaction progress and vinblastine yield by comparison with "one-shot" NADH addition of the same aggregate amount. For example, adding small amounts of NADH every fifteen minutes for three hours to the reaction has proved useful. It is possible NADH addition in staged amounts may be omitted when the reaction is supplied with an NADH regeneration system as described above. Simple experimentation wil be required in order to determine the best method of supplying NADH to the reaction.

Under the conditions exemplified herein, vinblastine formation is at a peak at around 2–5 hours. Variations of this time frame are possible depending on process conditions and its is suggested therefore that reaction progress is monitored to determine peak vinblastine formation. The reaction progress may then be halted by addition of a suitable base such as sodium hydroxide. Vinblastine formed by the reaction may then be recovered using standard extraction techniques (see, for example, Canadian Patent No. 948,625).

Embodiments of the invention are described hereinafter by way of example only.

EXAMPLE 1

Preparation of Crude Enzyme

Two-week old *C. roseus* suspension cells were harvested and frozen at −20° C. The frozen cells were ground in a chilled mortar with equivalent weight of wet PVPP and two volumes of Tris/HCl buffer (pH 6.8, 100 mM). The extract was centrifuged at 10,000 g for 20 minutes. Protein was precipitated from the supernatant with 70% saturated $(NH_4)_2SO_4$. The protein pellet was desalted with Bio-Gel p6 equilibrated with the same buffer. A solution of this protein fraction was frozen and stored at −20° C. and used in the research described in the following examples.

EXAMPLE 2

The effect of pH on the ability of various cofactors to influence vinblastine yield from enzyme-transformed AVLB was examined using two different buffering systems i.e. Tris-HCl to maintain pH at around 6.8 and potassium phosphate to maintain about pH 4.5. In this experiment, 2.5 ml buffer were mixed with 0.5 mg. AVLB, 0.25 ml of a leaf-extracted enzyme fraction (68.2 mg protein/ml buffer prepared in a manner similar to example 1) and sufficient $MnCl_2$ to provide a final $MnCl_2$ concentration of 1 mM. The reaction progressed at 30° C. for 4 hours. Aliquots of NADH and NADPH (0.2 mg in 0.1 ml buffer) were added to the admixture every 30 minutes for the first 2.5 hours. The vitamin $B_{12}$ was added, all at once. Vinblastine yields analyzed by TLC appear in Table 1:

TABLE 1

| Cofactor | Buffer | pH | VLB yield (μg) | % Yield VLB |
|---|---|---|---|---|
| Control | Tris-HCl | 6.8 | 5.3 | 1.1 |
| Vitamin $B_{12}$ | " | " | 2.5 | 0.5 |
| NADH | " | " | 34.4 | 6.9 |
| NADPH | " | " | 16.4 | 3.3 |
| Control | Phosphate | 4.5 | 1.3 | 0.2 |
| Vitamin $B_{12}$ | " | " | 2.1 | 0.4 |
| NADH | " | " | 10.9 | 2.2 |
| NADPH | " | " | 10.2 | 2.0 |

The results shown in Table 1 demonstrate that while vinblastine yeilds are enhanced by comparison with the control at either pH 4.5 or 6.8, best results are obtained at the higher, near-neutral pH. Also, while all cofactors influenced conversion favourably, the reduced nicotinamides gave better results than did vitamin $B_{12}$, a flavin derivative.

EXAMPLE 3

NADH Influence

Given the results appearing above, the effect specifically of various NADH amounts on vinblastine synthesis was measured against the NADH effect in the absence of enzyme using conditions and protocol substantially as described in Example 2 but with 0.4 mg AVLB. The reaction progressed until termination by addition of 25 μl concentrated ammonium hydroxide. The results appear below in Table 2.

TABLE 2

| Cofactor | Amount | VLB (μg) | % Yield |
|---|---|---|---|
| NADH | 0.4 mg | 26.6 | 6.7 |
| NADH | 0.2 mg | 19.6 | 4.9 |
| without enzyme | 0.4 mg | 2.9 | 0.7 |

It is clear that enzyme is necessary for optimum vinblastine production. It is also evident that NADH enhances vinblastine yield—as the amount of NADH relative to the amount of AVLB is increased, vinblastine yield increases when enzyme amount remains constant.

EXAMPLE 4

The effect of various divalent cationic species on the overall process was analyzed. In this series of experiments, a reaction medium consisted of the cationic species in the amount stated below in Table 3, 4 mg of protein obtained from *C. roseus* suspension cells as described in Example 1, 0.2 mg AVLB and a total NADH amount of 3.0 mg, added in 0.5 mg every 30 minutes until the reaction was terminated in the standard fashion after 3 hours. The results appear below in Table 3.

TABLE 3

| Cation Source | Concentration | VLB yield (μg) | % Yield |
|---|---|---|---|
| Control | — | 12.7 | 6.3 |
| $CaCl_2$ | 10 mM | 11.5 | 5.7 |
| $MgSO_4$ | 10 mM | 13.8 | 6.9 |
| $FeSO_4$ | 1 mM | N.D. | — |
| $FeCl_3$ | 1 mM | N.D. | — |
| $CoCl_2$ | 1 mM | 13.0 | 6.5 |
| $ZnSO_4$ | 1 mM | 5.7 | 2.8 |
| $CuSO_4$ | 1 mM | 12.6 | 6.3 |
| $NiCl_2$ | 1 mM | 9.6 | 4.8 |
| $MnCl_2$ | 1 mM | 19.3 | 9.7 |

By comparing the yield of VLB when the various cations are introduced with the control, it is apparent that the manganese ion provides the best results. It will also be noted that magnesium, cobalt and copper (cupric) ions may be used without inhibiting expected yield when NADH per se is added. Further, yields of VLB apparently decreased when nickel, calcium and zinc ions were used. Thus, it is preferred to avoid their use although VLB yield can still be reasonable should these ions contaminate the reaction to a minor extent. Use of ferrous or ferric ion is to be avoided. It will further be noted from these results that cofactor NADH, is able to enhance VLB yield even in the absence of cation.

EXAMPLE 5

MnCl₂ Influence

To analyze the effect of manganese ion on NADH influence in more detail, varying amounts of AVLB were treated with constant amounts of protein fraction (2.0 mg from suspension cells) and NADH (3.0 mg added in 0.5 mg aliquots every 30 minutes) and in the presence and absence of MnCl₂ (final concentration of 1 mM). The results appear in Table 4 below:

TABLE 4

| Amount of AVLB (mg) | MnCl₂ | VLB Yield (μg) | % Yield |
| --- | --- | --- | --- |
| 0.4 | + | 18.8 | 4.7 |
| 0.2 | + | 7.5 | 3.8 |
| 0.1 | + | 4.2 | 4.2 |
| 0.4 | − | 9.5 | 2.4 |
| 0.2 | − | 4.1 | 2.0 |
| 0.1 | − | 2.2 | 2.2 |

It is evident from the Table that the manganese ion affects favourable the yield of vinblastine, in the presence of NADH and enzyme. Under the experimental conditions, a 100% increased yield is realized.

EXAMPLE 6

NADH Addition

In order to enhance conversion of AVLB to VLB in the enzyme system, NADH is added. The method of adding NADH can vary from one-time addition of all NADH to be used, to a sequential additions of portions of the total amount to be added. On the basis of the results appearing below, it is preferred to add portions in succession e.g. every 30 minutes for 3-5 hours.

TABLE 5

| Amount of NADH | Total Time | Yield VLB (μg) | % Yield |
| --- | --- | --- | --- |
| 6 mg; 1 mg every 30 min. | 3 hours | 14.4 | 7.2 |
| 3 mg; 0.5 mg every 30 min. | 3 hours | 14.8 | 7.4 |
| 1.5 mg; 0.25 mg every 30 min. | 3 hours | 10.6 | 5.3 |
| 10 mg; 1 mg every 30 min. | 5 hours | 22.5 | 11.3 |
| 5 mg; 0.5 mg every 30 min. | 5 hours | 25.3 | 12.7 |
| 2.5 mg; 0.25 mg every 30 min. | 5 hours | 20.5 | 10.3 |

AVLB = 0.2 mg; tris-buffer; 0.1 ml (1 mM) MnCl₂; 0.2 mg enzyme

On the bases of further experimentation, it is apparent that the 5 hours protocol, with NADH addition every 30 minutes, may be replaced with a 3 hour, every 15 minute protocol to provide equivalent vinblastine yield under otherwise similar conditions.

EXAMPLE 7

In a refined experiment to determine optimum pH when NADH is used, 2.7 mg protein from suspension cells was reacted with 0.4 mg. AVLB in 1 mM MnCl₂ and a total of 0.5 mg NADH added in 50 μl aliquots every 30 minutes for 4.5 hours. The results, indicating a preferred pH at arounrd 7.5, are given below:

TABLE 6

| Buffer | pH | VLB yield (μg) | % Yield of VLB |
| --- | --- | --- | --- |
| MES | 5.7 | 14.2 | 3.6 |
|  | 6.3 | 27.5 | 6.9 |
|  | 6.8 | 33.5 | 8.4 |
| Tris | 6.8 | 33.4 | 8.4 |
|  | 7.5 | 48.9 | 12.2 |
|  | 8.2 | 39.6 | 9.9 |

Vinblastine produced in these experiments was analyzed by high resolution mass spectrophotometry which confirmed presence of vinblastine by comparison with a vinblastine standard. Presence of vinblastine has also been confirmed with HPLC. All results quoted above are the result of separating vinblastine with TLC using Silica (Si 250F plates) with a mobile phase of toluene:acetone:methanol:NH₄OH (85:30:6:1.5).

While the production of vinblastine is described herein, it will be appreciated that other alkaloid dimers are generated from the AVLB starting material. Also produced in detectable quantities are leurosine and possibly 3 R-OH vinamidine. Accordingly, the present process is also useful in generating other alkaloids but is tailored, in accordance with the preferred embodiments described herein, to generating vinblastine.

The mechanism of the reaction to produce vinblastine is not yet fully understood. While not intending to be bound by any particular theory, it is believed that enzyme derived from *C. roseus* oxidizes the AVLB to an iminium intermediate which is subsequently reduced, perhaps by the NADH, to vinblastine. It will be appreciated therefore, that in all likelihood, only certain oxidizing enzymes produced by *C. roseus* are involved in this conversion and once identified, may be used selectively in the process described herein i.e. together with a reducing agent such as NADH and optionally in the presence of a divalent cation such as manganese ion, to generate vinblastine. At present, the *C. roseus* extract merely represents one suitable source of the enzyme necessary for this reaction. Purified *C. roseus* enzymes or pure enzymes from other sources with similar activity will be useful herein, in combination with NADH, to produce vinblastine.

What is claimed is:

1. A method for enhancing vinblastine yield from a reaction in which 3', 4'-anhydrovinblastine and *C. roseus*-derived enzyme are reacted in a reaction medium to produce vinblastine, said method comprising the steps of:
   (a) adding to said reaction medium both NADH and a water soluble salt of a divalent cationic species selected from the group consisting of manganese, cobalt, copper and magnesium;
   (b) supplementing the reaction mixture formed in step (a) with NADH at a plurality of stages during the course of the reaction;
   (c) adding a reaction-halting amount of a base to the reaction medium prior to vinblastine recovery and at a time when vinblastine yields are maximal; and
   (d) then recovering vinblastine from the reaction medium.

2. The method of claim 1 wherein the base is sodium hydroxide.

3. The method claim 1 wherein the divalent cation species is manganese.

4. The method of claim 1 wherein NADH and said divalent cationic species are added in amounts sufficient to elevate yield of vinblastine by at least 50% relative to yields in the absence of said cationic species.

5. The method of claim 1 wherein the reaction medium is supplemented with a means for replenishing the supply of NADH therein.

* * * * *